United States Patent
Wang et al.

(10) Patent No.: US 10,087,127 B2
(45) Date of Patent: Oct. 2, 2018

(54) PROCESS FOR PRODUCING 2,3,3,3-TETRAFLUOROPROPENE

(71) Applicant: HONEYWELL INTERNATIONAL INC., Morristown, NJ (US)

(72) Inventors: Haiyou Wang, Amherst, NY (US); Hsueh Sung Tung, Getzville, NY (US)

(73) Assignee: HONEYWELL INTERNATIONAL INC., Morristown ( * ) Notice: Subject to any disclaimer, the term of this patent is extended or adjusted under 35 U.S.C. 154(b) by 0 days.

(21) Appl. No.: 15/350,725

(22) Filed: Nov. 14, 2016

(65) Prior Publication Data

US 2017/0057892 A1    Mar. 2, 2017

Related U.S. Application Data

(60) Division of application No. 14/348,804, filed as application No. PCT/US2012/058149 on Sep. 29, 2012, now Pat. No. 9,493,384, said application No. 14/348,804 is a continuation-in-part of application No. 12/167,159, filed on Jul. 2, 2008, now Pat. No. 9,040,759.

(60) Provisional application No. 61/541,552, filed on Sep. 30, 2011, provisional application No. 60/958,468, filed on Jul. 6, 2007.

(51) Int. Cl.
| | | |
|---|---|---|
| C07C 19/12 | (2006.01) |
| C07C 17/25 | (2006.01) |
| B01J 35/00 | (2006.01) |
| B01J 27/10 | (2006.01) |
| B01J 27/12 | (2006.01) |
| B01J 27/138 | (2006.01) |
| C07B 35/06 | (2006.01) |

(52) U.S. Cl.
CPC .............. C07C 19/12 (2013.01); B01J 27/10 (2013.01); B01J 27/12 (2013.01); B01J 27/138 (2013.01); B01J 35/0006 (2013.01); C07B 35/06 (2013.01); C07C 17/25 (2013.01)

(58) Field of Classification Search
None
See application file for complete search history.

(56) References Cited

U.S. PATENT DOCUMENTS

| | | | |
|---|---|---|---|
| 2,931,840 A | 4/1960 | Marquis |
| 4,900,874 A | 2/1990 | Ihara et al. |
| 5,162,594 A | 11/1992 | Krespan |
| 8,058,486 B2 | 11/2011 | Merkel et al. |
| 8,071,825 B2 | 12/2011 | Johnson et al. |
| 8,084,653 B2 | 12/2011 | Tung et al. |
| 2007/0197842 A1 | 8/2007 | Mukhopadhyay et al. |
| 2009/0030247 A1* | 1/2009 | Johnson .................. C07C 17/04 570/155 |
| 2009/0142837 A1 | 6/2009 | Adams, Jr. et al. |
| 2009/0240090 A1* | 9/2009 | Merkel ..................... C01B 7/035 570/160 |
| 2009/0287027 A1 | 11/2009 | Merkel et al. |
| 2010/0036179 A1 | 2/2010 | Merkel et al. |
| 2011/0105807 A1 | 5/2011 | Kopkalli et al. |
| 2011/0130599 A1 | 6/2011 | Elsheikh et al. |
| 2011/0160498 A1 | 8/2011 | Merkel et al. |
| 2011/0218369 A1 | 9/2011 | Elsheikh et al. |
| 2012/0232317 A1 | 9/2012 | Nappa |

FOREIGN PATENT DOCUMENTS

| | | |
|---|---|---|
| CN | 101440017 A | 5/2009 |
| CN | 101522597 A | 9/2009 |
| CN | 101597209 A | 12/2009 |
| CN | 101665403 A | 3/2010 |
| CN | 101684060 A | 3/2010 |
| EP | 2 119 692 A1 | 11/2009 |
| JP | 2009-298781 A | 12/2009 |
| WO | 2011/056441 A2 | 5/2011 |
| WO | WO 2011/087825 A1 | 7/2011 |

OTHER PUBLICATIONS

Notification of Reasons for Rejection dated Jan. 31, 2017 issued in Japanese Application No. 2014-533445.
Banks, R. E., et al., "Preparation of 2,3,3,3-tetrafluoropropene from trifluoroacetylacetone and sulphur tetrafluoride" Journal of Fluorine Chemistry 82:171-174 (1997).
Chinese First Office Action and Search Report issued in Chinese Patent Application No. 201280057971.9 dated Nov. 15, 2014 in English and in Chinese.
Chinese Second Office Action and Search Report issued in Chinese Patent Application No. 201280057971.9 dated Sep. 15, 2015 (in English and in Chinese).
Gang, S., "Study on the patent of 2,3,3,3-tetrafluoropropene" Organo-Fluorine Industry 2:35-44 (2009) English abstract only.
International Search Report dated Jan. 2, 2013 issued in PCT/US2012/058149.
Japanese Official Action dated May 11, 2016 from related JP 2014-533445 together with English language translation.
Supplementary Partial European Search Report issued on Application No. EP 12 83 5833 dated Jul. 2, 2015.
Communication pursuant to Article 94(3) EPC issued in European Patent Application No. 12 835 833.0 dated Feb. 20, 2017.

* cited by examiner

*Primary Examiner* — Clinton A Brooks
(74) *Attorney, Agent, or Firm* — Scully Scott Murphy and Presser

(57) ABSTRACT

The present invention relates, in part, to the discovery that the presence of HF in a HCFC-244bb feedstream in a reaction for the preparation of HFO-1234yf results in selectivity changeover from HFO-1234yf to HCFO-1233xf. By substantially removing HF, it is shown that the selectivity to HFO-1234yf via dehydrochlorination of HCFC-244bb is improved.

13 Claims, No Drawings

PROCESS FOR PRODUCING 2,3,3,3-TETRAFLUOROPROPENE

CROSS REFERENCES TO RELATED APPLICATIONS

This application is a divisional of U.S. patent application Ser. No. 14/348,804, filed Mar. 31, 2014, now U.S. Pat. No. 9,493,384, issuing on Nov. 15, 2016, which is a '371 of International Patent Application No. PCT/US2012/058149 filed Sep. 29, 2012, which claims benefit of U.S. Provisional Application No. 61/541,552 filed Sep. 30, 2011, the contents of which are incorporation by reference. This application is also a continuation-in-part of U.S. patent application Ser. No. 12/167,159, filed Jul. 2, 2008, now U.S. Pat. No. 9,040,759 filed May 26, 2015, which claims benefit of U.S. Provisional Application No. 60/958,468, filed Jul. 6, 2007, the contents each of which are incorporated herein by reference.

FIELD OF INVENTION

This invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

Other art showing the formation of fluorinated olefins includes U.S. Pat. Nos. 8,071,825, 8,058,486 and 8,084,653, the contents of all of which are incorporated by reference.

However, there remains a need for an economic means of producing hydrofluoroolefins, such as HFO-1234yf. The present invention satisfies this need among others.

SUMMARY OF THE INVENTION

The present invention relates, in part, to the surprising discovery that, during the dehydrochlorination of HCFC-244bb to HFO-1234yf, the presence of HF in HCFC-244bb feedstock leads to selectivity changeover from HFO-1234yf to HCFO-1233xf, i.e., selectivity of HFO-1234yf is decreased and selectivity to HCFO-1233xf is increased. Accordingly, the present invention relates to methods of improving HFO-1234yf selectivity by reducing the presence of HF in the HCFC-244bb feed stream and avoiding, or at least reducing, the formation of HCFO-1233xf.

In one aspect, the present invention relates to a feedstock for use in preparing a fluoroolefin, wherein the feedstock comprises HCFC-244bb and is substantially free of HF. While the definition of "substantially free" may be as defined herein, in one aspect, the feedstock is substantially free of HF when HF is present in the composition in an amount less than about 5000 ppm, less than about 500 ppm, less than about 50 ppm, or is completely free of HF.

In another aspect, the present invention relates to a method for reducing the level of HF within a HCFC-244 feedstock by providing a composition comprising 2-chloro-1,1,1,2-tetrafluoropropane, and reducing the level of HF such that it is substantially free of HF. In one embodiment, HF may be reduced by distillation. In another embodiment, HF may be reduced by passing the composition through a scrubber charged with a caustic solution. Such a caustic solution may be selected from the group KOH, NaOH, $Ca(OH)_2$, or CaO. In yet another embodiment, the HF may be reduced by passing the composition over a solid sorbent. Such a solid sorbent may be selected from the group consisting of alumina, calcium carbonate, sodium carbonate, and sodium aluminate and the like.

In another aspect, the present invention relates to a process for preparing HFO-1234yf by providing a starting composition including HCFC-244bb that is substantially free of HF and contacting said starting composition with a dehydrochlorination catalyst to produce a final composition comprising HFO-1234yf. In certain embodiments, the dehydrochlorination catalyst is selected from the group consisting of (i) one or more metal halides, (ii) one or more halogenated metal oxides, (iii) one or more zero-valent metals/metal alloys, and (iv) a combination of two or more of these. By using a HCFC-244bb feedstock that is substantially free of HF, selectivity to HFO-1234yf can be at least 90% or higher, 95% or higher, or 97% or higher.

In even further aspects, the present invention relates to a process for preparing 2,3,3,3-tetrafluoropropene by:

(i) providing a starting composition including a compound of Formulas I, II, or III:

 (I);

 (II); or

 (III)

wherein X is independently selected from F, Cl, Br, and I, provided that at least one X is not fluorine;
(ii) contacting the starting composition with a first fluorinating agent to produce a first intermediate composition including 2-chloro-3,3,3-trifluoropropene and a first chlorine-containing byproduct;
(iii) contacting the first intermediate composition with a second fluorinating agent to produce a second intermediate composition including 2-chloro-1,1,1,2-tetrafluoropropane and HF;
(iv) reducing the level of HF in the second intermediate composition to produce a third intermediate composition including 2-chloro-1,1,1,2-tetrafluoropropane that is substantially free of HF; and
(v) dehydrochlorinating at least a portion of the 2-chloro-1,1,1,2-tetrafluoropropane to produce a reaction product including 2,3,3,3-tetrafluoropropene.

In certain embodiments, HF is present in the third intermediate composition in an amount less than about 5000 ppm, less than about 500 ppm, less than about 50 ppm. In certain embodiments, the selectivity for 2,3,3,3-tetrafluoropropene in step (v) is at least 90% or higher, 95% or higher, or 97% or higher.

Additional embodiments and advantages to the present invention will be readily apparent to one of skill in the art, based on the disclosure provided herein.

DETAILED DESCRIPTION OF PREFERRED EMBODIMENTS

According to one embodiment, the present invention relates to a manufacturing process for making HFO-1234yf using a starting or intermediate material comprising HCFC-244b that is substantially free of HF. Applicants have surprisingly found that the presence of HF decreases selective conversion of HCFC-244bb to HFO-1234yf. Accordingly, the present invention provides methods of removing HF from such material to improve the overall efficiency of the HFO-1234yf conversion process.

In certain aspects, the preparation of HFO-1234yf generally includes at least three reaction steps, as follows:
(i) ($CX_2$=CCl—$CH_2X$ or $CX_3$—CCl=$CH_2$ or $CX_3$—CHCl—$CH_2CX$)+HF→2-chloro-3,3,3-trifluoropropene (HCFO-1233xf)+HCl in a vapor phase reactor charged with a solid catalyst;
(ii) 2-chloro-3,3,3-trifluoropropene (HCFO-1233xf)+HF→2-chloro-1,1,1,2-tetrafluoropropane (HCFC-244bb) in a liquid phase reactor charged with a liquid hydrofluorination catalyst; and
(iii) 2-chloro-1,1,1,2-tetrafluoropropane (HCFC-244bb)→2,3,3,3-tetrafluoropropene (HFO-1234yf) in a vapor phase reactor.
wherein X is independently selected from F, Cl, Br, and I, provided that at least one X is not fluorine.

The starting material in the first reaction step is one or more chlorinated compounds according to Formulas I, II, and/or III:

  (Formula I)

  (Formula II)

  (Formula III)

wherein X is independently selected from F, Cl, Br, and I, provided that at least one X is not fluorine. In certain embodiments, these compounds contain at least one chlorine, a majority of X is chlorine, or all X is chlorine.

In the first step, the starting composition (which, in certain embodiments comprises 1,1,2,3-tetrachloropropene (1230xa) and/or 1,1,1,2,3-pentachloropropane (HCC-240db)) reacts with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, heavy intermediates, HFC-245cb, or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel, and the like. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/carbon, $CoCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction and may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuous, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

In the second step of the process for forming 2,3,3,3-tetrafluoropropene, HCFO-1233xf is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, Inconel 625, and the like.

Preferred, but non-limiting, catalysts include activated carbon, stainless steel (e.g., SS 316), austenitic nickel-based alloys (e.g., Inconel 625), nickel, fluorinated 10% CsCl/MgO, 10% $CsCl/MgF_2$ and the like. A suitable reaction temperature is about 300-550° C. and a suitable reaction pressure may be between about 0-150 psig. The reactor effluent may be fed to a caustic scrubber or to a distillation column to remove the byproduct of HCl to produce an acid-free organic product which, optionally, may undergo further purification using one or any combination of purification techniques that are known in the art.

The reaction may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

The present inventors have surprisingly discovered that, during the dehydrochlorination of HCFC-244bb to form HFO-1234yf, the presence of HF in the HCFC-244bb feedstock decreases the selectivity to HFO-1234yf and increases selectivity toward HCFO-1233xf, which is an undesired byproduct. While not intending to be bound by theory, it is believed that metal fluorides such as $NiF_2$, $CrF_3$, $FeF_3$, and the like, are incidentally formed by the reaction of HF with metal components of the reactor (e.g., Inconel 625). These metal fluorides, especially trivalent metal fluorides, act as dehydrofluorination catalysts converting HCFC-244bb back to HCFO-1233xf. The present invention provides a solution to this problem by reducing the content of HF in the HCFC-244bb feed stream, thereby improving HFO-1234yf selectivity and similarly reducing the formation of HCFO-1233xf.

To this end, and prior to the third reaction step, the composition comprising HCFC-244bb is first purified to form a starting feedstock that is substantially free of HF. As used herein, the definition of "substantially free" means that the amount of HF is reduced in the HCFC-244bb feedstream so as to measurably improve selectivity of the conversion of HCFC-244bb to HFO-1234yf and/or decrease selectivity in the conversion of HCFC-244bb to HCFO-1233xf. In one aspect, HF is provided in the purified feedstock of HCFC-244bb in an amount less than about 5000 ppm, less than about 500 ppm, less than about 50 ppm, or is completely free of HF. In another embodiment, the HF is provided in the purified feedstock of HCFC-244bb in an amount of less than about 2500 ppm; less than about 1000 ppm; less than about 900 ppm; less than about 800 ppm; less than about 700 ppm; less than about 600 ppm; less than about 400 ppm; less than about 300 ppm; less than about 200 ppm; less than about 100 ppm; less than about 90 ppm, less than about 80 ppm, less than about 70 ppm, less than about 60 ppm; less than about 40 ppm; less than about 30 ppm; less than about 20 ppm; or less than about 10 ppm. In other embodiments, the HF is present in the HCFC-244bb feedstock in concentrations ranging from about 0 ppm to about 5,000 ppm and in another embodiment, from about 0 ppm to about 1000 ppm, and in another embodiment from about 0 ppm to about 500 ppm. In still other embodiment, the HF is present in the feedstock of HCFC-244bb in an amount of 500 ppm, 499 ppm, 498 ppm, 497 ppm, 496 ppm, 495 ppm, 494 ppm, 493 ppm, 492 ppm, 491 ppm, 490 ppm, 489 ppm, 488 ppm, 487 ppm, 486 ppm, 485 ppm, 484 ppm, 483 ppm, 482 ppm, 481 ppm, 480 ppm, 479 ppm, 478 ppm, 477 ppm, 476 ppm, 475 ppm, 474 ppm, 473 ppm, 472 ppm, 471 ppm, 470 ppm, 469 ppm, 468 ppm, 467 ppm, 466 ppm, 465 ppm, 464 ppm, 463 ppm, 462 ppm, 461 ppm, 460 ppm, 459 ppm, 458 ppm, 457 ppm, 456 ppm, 455 ppm, 454 ppm, 453 ppm, 452 ppm, 451 ppm, 450 ppm, 449 ppm, 448 ppm, 447 ppm, 446 ppm, 445 ppm, 444 ppm, 443 ppm, 442 ppm, 441 ppm, 440 ppm, 439 ppm, 438 ppm, 437 ppm, 436 ppm, 435 ppm, 434 ppm, 433 ppm, 432 ppm, 431 ppm, 430 ppm, 429 ppm, 428 ppm, 427 ppm, 426 ppm, 425 pm, 424 ppm, 423 ppm, 422 ppm, 421 ppm, 420 ppm, 419 ppm, 418 ppm, 417 ppm, 416 ppm, 415 ppm, 414 ppm, 413 ppm, 412 ppm, 411 ppm, 410 ppm, 409 ppm, 408 ppm, 407 ppm, 406 ppm, 405 ppm, 404 ppm, 403 ppm, 402 ppm 401 ppm, 400 ppm, 399 ppm, 398 ppm, 397 ppm, 396 ppm, 395 ppm, 394 ppm, 393 ppm, 392 ppm, 391 ppm, 390 ppm, 389 ppm, 388 ppm, 387 ppm, 386 ppm, 385 ppm, 384 ppm, 383 ppm, 382 ppm, 381 ppm, 380 ppm, 379 ppm, 378 ppm, 377 ppm, 376 ppm, 375 ppm, 374 ppm, 373 ppm, 372 ppm, 371 ppm, 370 ppm, 369 ppm, 368 ppm, 367 ppm, 366 ppm, 365 ppm, 364 ppm, 363 ppm, 362 ppm, 361 ppm, 360 ppm, 359 ppm, 358 ppm, 357 ppm, 356 ppm, 355 ppm, 354 ppm, 353 ppm, 352 ppm, 351 ppm, 350 ppm, 349 ppm, 348 ppm, 347 ppm, 346 ppm, 345 ppm, 344 ppm, 343 ppm, 342 ppm, 341 ppm, 340 ppm, 339 ppm, 338 ppm, 337 ppm, 336 ppm, 335 ppm, 334 ppm, 333 ppm, 332 ppm, 331 ppm, 330 ppm, 329 ppm, 328 ppm, 327 ppm, 326 ppm, 325 ppm, 324 ppm, 323 ppm, 322 ppm, 321 ppm, 320 ppm, 319 ppm, 318 ppm, 317 ppm, 316 ppm, 315 ppm, 314 ppm, 313 ppm, 312 ppm, 311 ppm, 310 ppm, 309 ppm, 308 ppm, 307 ppm, 306 ppm, 305 ppm, 304 ppm, 303 ppm, 302 ppm, 301 ppm, 300 ppm, 299 ppm, 298 ppm, 297 ppm, 296 ppm, 295 ppm, 294 ppm, 293 ppm, 292 ppm, 291 ppm, 290 ppm, 289 ppm, 288 ppm, 287 ppm, 286 ppm, 285 ppm, 284 ppm, 283 ppm, 282 ppm, 281 ppm, 280 ppm, 279 ppm, 278 ppm, 277 ppm, 276 ppm, 275 ppm, 274 ppm, 273 ppm, 272 ppm, 271 ppm, 270 ppm, 269 ppm, 268 ppm, 267 ppm, 266 ppm, 265 ppm, 264 ppm, 263 ppm, 262 ppm, 261 ppm, 260 ppm, 259 ppm, 258 ppm, 257 ppm, 256 ppm, 255 ppm, 254 ppm, 253 ppm, 252 ppm, 251 ppm, 250 ppm, 249 ppm, 248 ppm, 247 ppm, 246 ppm, 245 ppm, 244 ppm, 243 ppm, 242 ppm, 241 ppm, 240 ppm, 239 ppm, 238 ppm, 237 ppm, 236 ppm, 235 ppm, 234 ppm, 233 ppm, 232 ppm, 231 ppm, 230 ppm, 229 ppm, 228 ppm, 227 ppm, 226 ppm, 225 ppm, 224 ppm, 223 ppm, 222 ppm, 221 ppm, 220 ppm, 219 ppm, 218 ppm, 217 ppm, 216 ppm, 215 ppm, 214 ppm, 213 ppm, 212 ppm, 211 ppm, 210 ppm, 209 ppm, 208 ppm, 207 ppm, 206 ppm, 205 ppm, 204 ppm, 203 ppm, 202 ppm, 201 ppm, 200 ppm, 199 ppm, 198 ppm, 197 ppm, 196 ppm, 195 ppm, 194 ppm, 193 ppm, 192 ppm, 191 ppm, 190 ppm, 189 ppm, 188 ppm, 187 ppm, 186 ppm, 185 ppm, 184 ppm, 183 ppm, 182 ppm, 181 ppm, 180 ppm, 179 ppm, 178 ppm, 177 ppm, 176 ppm, 175 ppm, 174 ppm, 173 ppm, 172 ppm, 171 ppm, 170 ppm, 169 ppm, 168 ppm, 167 ppm, 166 ppm, 165 ppm, 164 ppm, 163 ppm, 162 ppm, 161 ppm, 160 ppm, 159 ppm, 158 ppm, 157 ppm, 156 ppm, 155 ppm, 154 ppm, 153 ppm, 152 ppm, 151 ppm, 150 ppm, 149 ppm, 148 ppm, 147 ppm, 146 ppm, 145 ppm, 144 ppm, 143 ppm, 142 ppm, 141 ppm, 140 ppm, 139 ppm, 138 ppm, 137 ppm, 136 ppm, 135 ppm, 134 ppm, 133 ppm, 132 ppm, 131 ppm, 130 ppm, 129 ppm, 128 ppm, 127 ppm, 126 ppm, 125 ppm, 124 ppm, 123 ppm, 122 ppm, 121 ppm, 120 ppm, 119 ppm, 118 ppm, 117 ppm, 116 ppm, 115 ppm, 114 ppm, 113 ppm, 112 ppm, 111 ppm, 110 ppm, 109 ppm, 108 ppm, 107 ppm, 106 ppm, 105 ppm 104 ppm 103 ppm, 102 ppm, 101 ppm, 100 ppm, 99 ppm, 98 ppm, 97 ppm, 96 ppm, 95 ppm, 94 ppm, 93 ppm, 92 ppm, 91 ppm, 90 ppm, 89 ppm, 88 ppm, 87 ppm, 86 ppm, 85 ppm, 84 ppm, 83 ppm, 82 ppm, 81 ppm, 80 ppm, 79 ppm, 78 ppm, 77 ppm, 76 ppm, 75 ppm, 74 ppm, 73 ppm, 72 ppm 71 ppm, 70 ppm, 69 ppm, 68 ppm, 67 ppm, 66 ppm, 65 ppm, 64 ppm, 63 ppm, 62 ppm, 61 ppm, 60 ppm, 59 ppm, 58 ppm, 57 ppm, 56 ppm, 55 ppm, 54 ppm, 53 ppm, 52 ppm, 51 ppm, 50 ppm, 49 ppm, 48 ppm, 47 ppm, 46 ppm, 45 ppm, 44 ppm, 43 ppm, 42 ppm, 41 ppm, 40 ppm, 39 ppm, 38 ppm, 37 ppm, 36 ppm, 35 ppm, 34 ppm, 33 ppm, 32 ppm, 31 ppm, 30 ppm, 29 ppm, 28 ppm, 27 ppm, 26 ppm, 25 pm, 24 ppm, 23 ppm, 22 ppm, 21 ppm, 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm, or 0 ppm. In another embodiment, the HF is present in the purified feedstock of HCFC-244bb in trace amounts. i.e., that is in amounts greater than 0 ppm but less than 1 ppm. Such compositions as described herein, in certain aspects, improve selectivity of HCFC-244bb to HFO-1234yf to at least 90% or higher, 95% or higher, or 97% or higher. Selectivity may be calculated by number of moles of product (HFO-1234yf) formed divided by number of moles of reactant consumed or, otherwise, using standard methods known in the art.

The amount of HF present in the HCFC-244bb is determined using standard techniques known in the art. For example, the amount of HF present is determined using known methods by GC or HPLC together with acid-base titration or IC (ion Chromatography).

Any techniques known in the art can be used to purify the HCFC-244bb intermediate. In one embodiment, HF is removed by distillation. Single column or multiple columns may be used. In another embodiment, HF is removed from a gaseous HCFC-244bb stream by passing the stream through a scrubber charged with an aqueous caustic solution, which is essentially a liquid (whether a solution, dispersion, emulsion, or suspension and the like). In certain embodiments, the caustic solution is an aqueous solution of a base selected from the group consisting of KOH, NaOH, Ca(OH)$_2$, CaO, and the like. Alternatively, the HF is removed from gaseous HCFC 244bb stream through a scrubber charged with a buffer having a pH ranging from about 7.0 to about 9.0. Examples include phosphate buffer, sodium carbonate buffer, and the like. In another embodiment, HF is removed from the gaseous HCFC-244bb stream by purging the stream through an adsorbent, such as molecular sieves, e.g., 3A, 4A, 5A, 13x and the like. The stream exiting from the caustic scrubber is fed into drying columns for moisture removal before being fed into the HCFC-244bb dehydrochlorination reactor. In yet another embodiment, the removal of HF from a liquid or gaseous HCFC-244bb stream is achieved by passing the stream over pre-packaged solid sorbents. Non-limiting solid sorbents include alumina, calcium carbonate, sodium carbonate, sodium aluminate, and the like. After HF is removed from HCFC-244bb stream, a substantially HF free HCFC-244bb feedstock is obtained.

In general, the effluent from the dehydrochlorination reactor may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used, HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

The following are examples of the invention and are not to be construed as limiting.

EXAMPLES

Example 1

This example illustrates the continuous vapor phase dehydrochlorination reaction of HCFC-244bb to HFO-1234yf with HCFC-244bb feedstock containing about 10 ppm HF.

The experiments were conducted in a bench scale pilot plant, which consists of $N_2$, organic feed, recycle feed, feed vaporizers, 1" (I.D.) U-shaped Inconel 625 reactor, distillation column, caustic scrubber, drying column, and product collection system. For continuous operation with recycle, fresh organic stream and organic recycle stream were combined before being fed into vaporizers and then reactor for reaction. The inner surface of the Inconel 625 reactor serves as dehydrochlorination catalyst. The reaction effluent was directed to a distillation for separation. The bottom stream, which mainly comprises HCFC-244bb and HCFO-1233xf, was sent back as recycle stream to be mixed with fresh HCFC-244bb feed; the overhead stream, which mainly comprises HFO-1234yf and HCl, was sent to KOH scrubber for acid removal. The acid-free product was then sent to a Dririte column for moisture removal before being compressed into a PCC (Product Collection Cylinder).

The reaction was conducted under conditions of 480° C., 50 psig, and 1 lb-organic/h. The mixed feed contained 93-98 GC area % HCFC-244bb and 2-7 GC area % HCFO-1233xf, as well as about 10 ppm HF. The reactor effluent was periodically analyzed by means of GC (Gas Chromatograph). The reaction was run for over 2000 hours. The GC analysis indicated that over the entire period of time HCFC-244bb conversion, HFO-1234yf selectivity, and HCFO-1233xf selectivity remained around 30%, 99.5%, and 0.5%, respectively. No selectivity changeover from HFO-1234yf to HCFO-1233xf took place.

Example 2

This example illustrates effect of HF in the feed on dramatic selectivity changeover for dehalogenation of HCFC-244bb. When the reactor, made of Inconel 625, is exposed to HF which is presence in the feed stream, it can cause selectivity changeover from the desired dehydrochlorination to make HFO-1234yf to the undesirable dehydrofluorination to make HCFO-1233xf during dehydrohalogenation.

The same reaction system as described in Example 1 was used except that a 2" Inconel reactor was used. The reactor was heated to 480° C. in $N_2$ flow (~1 L/min) The mixed HF/$N_2$ flow was then started by bubbling $N_2$ flow (~1 L/min) through the dip tube of an HF cylinder. After 10 hours, the HF was stopped and the reactor was purged in $N_2$ flow (~1 L/min) for 1 h. In total, 4.5 lbs of HF was consumed. The HCFC-244bb dehydrohalogenation reaction was then started with a feedstock containing 99.1 GC area % HCFC-244bb and 0.9 GC area % HCFO-1233xf under conditions of 480° C., 1 atm, and 1 lb organic/h. The GC analysis of reactor effluent samples shows that the HFO-1234yf selectivity was below 25%, while HCFO-1233xf selectivity was above 70%, indicating the effect of HF exposure of the reactor to HF causes the occurrence of selectivity changeover from desired HFO-1234yf to the undesired HCFO-1233xf.

The process on-stream time before the selectivity changeover (from HFO-1234yf to HCFO-1233xf) to occur depends on how much HF the reactor has been exposed to. This on-stream time can be calculated based on HF concentration coming in with the feed. As shown in Table 1, for HF concentration ≥5000 ppm, the run length was less than 1080 hours (one and half months), but it was longer than a year for HF concentration ≤500 ppm.

TABLE 1

Calculated run length with HF-containing 244bb feed at a feed rate of 1 lb/h

| HF concentration in feed stream | Time for selectivity changeover (from HFO-1234yf to HCFO-1233xf) to occur, h |
|---|---|
| 3.0 wt % | 170 |
| 2.0 wt % | 255 |
| 1.0 wt % | 510 |
| 5000 ppm | 1021 |
| 2000 ppm | 2552 |
| 1000 ppm | 5104 |
| 500 ppm | 10207 |
| 200 ppm | 25518 |
| 100 ppm | 51035 |
| 50 ppm | 1022070 |

It was surprising as to the effect that reducing the HF concentration with the HCFC-244bb fed into the reactor would have on the dehydrochlorination reaction before the on-stream time selectivity changeover (from HFO-1234yf to HCFO-1233xf) occurs. When the HF concentration is 5000 ppm, it takes about 1.5 months before the on-stream time selectivity changeover (from HFO-1234yf to HCFO-1233xf) occurs. However, reducing the concentration of HF 10 times to 500 ppm, it takes over 1 year before the on-stream time selectivity changeover (from HFO-1234yf to HCFO-1233xf) occurs. But when the HF concentration is reduced to 50 ppm, another 10 times, it takes almost 14 years before the on-stream time selectivity changeover (from HFO-1234yf to HCFO-1233xf) occurs. In other words, by reducing the amount of HF associated with HCFC-244bb, a methiod has been found to increase the lifetime of the dehydrochlorination reaction. i.e. reducing the tendency for the dehydrofluorination reaction to form HCFO-1233xf. This is significant, as no one has realized heretofore, this effect of reducing the amount of HF on the dehydrochlorination reaction.

Example 3

This example is prophetic. In a separate experiment, the same reaction system as described in Example 1 is used. All parameters are the same as in Example 1 except that additional HF is co-fed into the reactor together with organic feedstock at a rate of 14 g/min. The HF concentration in the combined HF and organic feedstock is about 3%. The GC analysis shows after 1 h on stream HCFC-244bb conversion is 30.0%; and HFO-1234yf selectivity, and HCFO-1233xf selectivity are about 99.5% and 0.5%, respectively; after 170 hours on stream the selectivity of HFO-1234yf and HCFO-1233xf changes to about 5.5% and 94.5%, respectively while HCFC-244bb conversion becomes 99.9%. A selectivity changeover from HFO-1234yf to HCFO-1233xf takes place. The reactor surface and internals have to be regenerated.

The above preferred embodiments and examples were given to illustrate the scope and spirit of the present invention. These embodiments and examples will make apparent to those skilled in the art other embodiments and examples. The other embodiments and examples are within the contemplation of the present invention. Therefore, the present invention should be limited only by the amended claims

What is claimed is:

1. A composition comprising 2-chloro-1,1,1,2-tetrafluoropropane, HF and a material selected from scrubber charged with a buffer having a pH ranging from about 7.0 to about 9.0, an aqueous caustic solution, an adsorbent and sorbent selected from alumina, calcium carbonate, sodium carbonate, and sodium aluminate, said material reducing the concentration of HF in said composition, such that when the material is separated from said composition, the concentration of HF ranges from 0 ppm, excluding 0 ppm, to 500 ppm.

2. The composition according to claim 1 wherein the concentration of HF in the composition separated from said material ranges from 0 ppm, excluding 0 ppm, to about 400 ppm.

3. The composition according to claim 1 wherein the concentration of HF in the composition separated from said material ranges from 0 ppm, excluding 0 ppm, to about 100 ppm.

4. The composition according to claim 1 wherein the concentration of HF in the composition separated from said material ranges from 0 ppm, excluding 0 ppm, to about 80 ppm.

5. The composition according to claim 1 wherein the concentration of HF in the composition separated from said material ranges from 0 ppm, excluding 0 ppm, to about 50 ppm.

6. The composition according to claim 1 wherein the concentration of HF in the composition separated from said material ranges from 0 ppm, excluding 0 ppm, to about 20 ppm.

7. The composition according to claim 1 wherein the concentration of HF in the composition separated from said material ranges from 0 ppm, excluding 0 ppm, to about 10 ppm.

8. The composition according to claim 1 wherein the caustic solution is an aqueous solution of KOH, NaOH, $Ca(OH)_2$ or CaO.

9. The composition according to claim 1 wherein the buffer is a phosphate buffer or sodium carbonate buffer.

10. The composition according to claim 1 wherein the adsorbent is a molecular sieve.

11. The composition according to claim 10 wherein the molecular sieve is 3A, 4A, 5A or 13X.

12. The composition according to claim 1 wherein the material is the solid sorbent.

13. The composition according to claim 1 wherein the material is selected from scrubber charged with a buffer having a pH ranging from about 7.0 to about 9.0, an adsorbent and sorbent selected from alumina, calcium carbonate, sodium carbonate, and sodium aluminate.

* * * * *